United States Patent [19]

Greenfield

[11] Patent Number: 5,584,835
[45] Date of Patent: Dec. 17, 1996

[54] SOFT TISSUE TO BONE FIXATION DEVICE AND METHOD

[76] Inventor: Jon B. Greenfield, 691 Loring Ave., Los Angeles, Calif. 90024

[21] Appl. No.: 303,016

[22] Filed: Sep. 8, 1994

Related U.S. Application Data

[63] Continuation of Ser. No. 137,259, Oct. 18, 1993, abandoned.

[51] Int. Cl.$^6$ ........................................... A61B 17/68
[52] U.S. Cl. ........................... 606/73; 606/72; 606/232
[58] Field of Search .............................. 606/232, 72, 73, 606/75; 24/625, 616, 459; 411/178, 403, 405, 395

[56] References Cited

U.S. PATENT DOCUMENTS

| | | | |
|---|---|---|---|
| 4,118,838 | 10/1978 | Schiefer et al. | 24/459 |
| 4,532,926 | 8/1985 | O'Holla . | |
| 4,898,156 | 2/1990 | Gatturna et al. | 606/72 |
| 4,899,743 | 2/1990 | Nicholson et al. | 606/139 |
| 4,946,468 | 8/1990 | Li | 606/232 |
| 5,002,550 | 3/1991 | Li | 606/139 |
| 5,156,616 | 10/1992 | Meadows et al. | 606/232 |
| 5,268,001 | 12/1993 | Nicholson et al. | 606/72 |
| 5,380,334 | 1/1995 | Torrie et al. | 606/75 |

FOREIGN PATENT DOCUMENTS

| | | | |
|---|---|---|---|
| 191081 | 8/1957 | Germany | 606/73 |
| 222047 | 9/1924 | United Kingdom | 411/178 |

OTHER PUBLICATIONS

Brochure–"Mitek Quick Anchor," Mitek Surgical Products, Norwood Mass. (Copyright 1990) author unknown.
Article—"Edoscopic Technique for ACL Reconstruction With Pro–Trac Tibial Guide: Endobutton Fixation," by Thomas D. Rosenberd, M.D. and Thomas Graf, M.D., Acuflex Microsurgical, Inc., Mansfield, MA (date unknown).
Brochure—"GII Anchor System—One System for Orthopaedic Soft Tissue Reattachment," Mitek Surgical Products, Norwood, Mass. (Copyright 1992) author unknown.

Brochure—"QuickAnchor™ The Name Says It All," Mitek Surgical Products, Norwood, Mass. (Aug. 1992) author unknown.

Brochure–"GII Anchor System—One System for Orthopaedic Soft Tissue Reattachment," Mitek Surgical Products, Norwood, Mass. (Mar. 1992) author unknown.

Article—"Arthroscopic Bankart Repair Using a Cannulated, Absorbable Fixation Device," by Warner and Warren, Operative Techniques in Orthopaedics, vol. 1, No. 2, pp. 192–198, Apr. 1991.

*Primary Examiner*—Guy V. Tucker
*Attorney, Agent, or Firm*—Rohm & Monsanto

[57] ABSTRACT

A two-part device for suturing soft tissue to bone employs a bone anchor which is installed in the bone and a suture anchor which is coupled to the soft tissue and then engaged with the bone anchor. The engagement of the suture anchor with the bone anchor is readily reversible so as to permit adjustments in the placement of the sutures. In the practice of the invention, no step is irreversible except the drilling of the bone hole that accepts the bone anchor. A special tool is described for facilitating the installation of a bone anchor having a round internal cross-section. The suture anchor can be installed with the application of only direct pressure, and can be disengaged by counterclockwise rotation, with the use of a disengagement tool, such as a screw driver. Sutures are threaded through apertures in the suture anchor, and the engagement of the sutures is enhanced by a friction fit between the suture and bone anchors.

26 Claims, 11 Drawing Sheets

FIG. 14
FIG. 17  FIG. 18
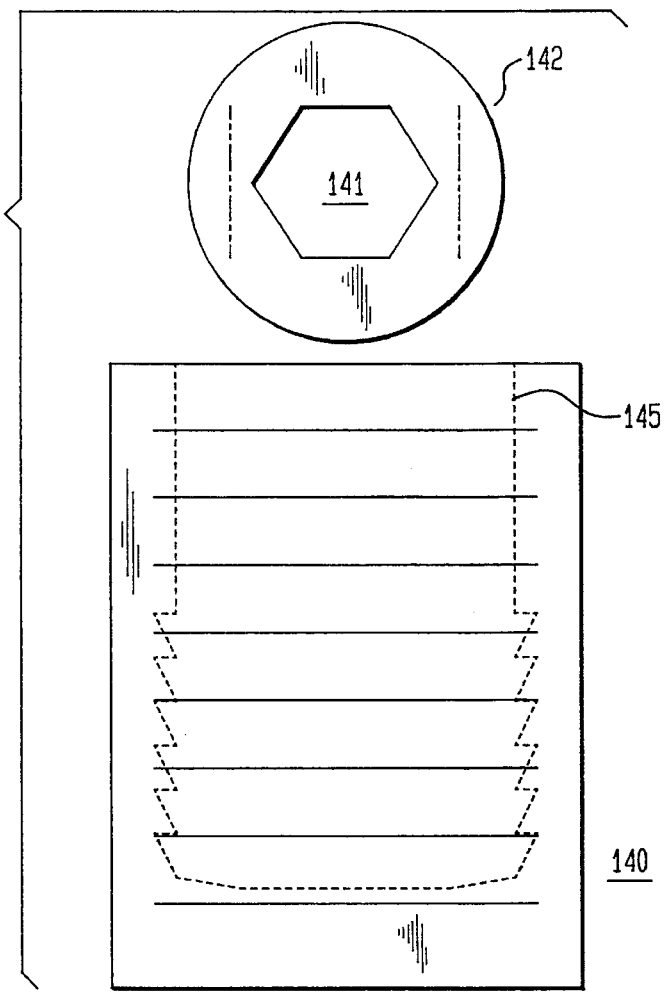
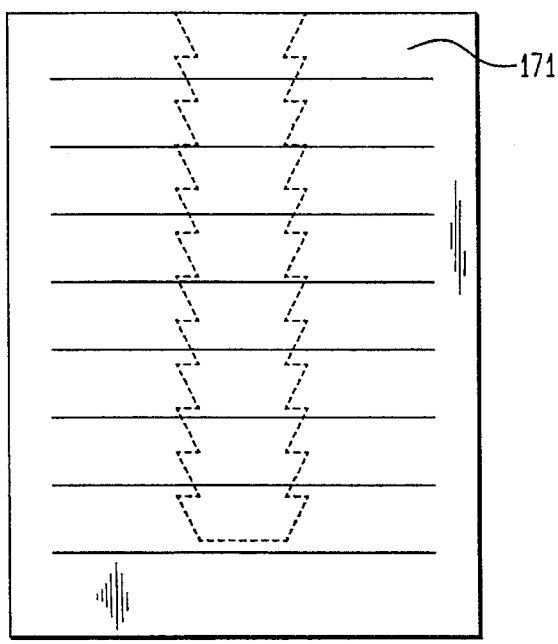
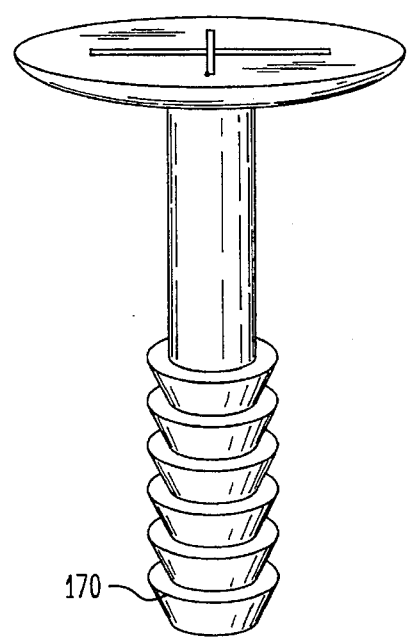

SOFT TISSUE TO BONE FIXATION DEVICE AND METHOD

RELATIONSHIP TO OTHER APPLICATION(S)

This application is a continuation of U.S. Ser. No. 08/137,259, filed Oct. 18, 1993, now abandoned, the disclosure of which is incorporated herein by reference.

BACKGROUND OF THE INVENTION

1. Field of the Invention

This invention relates generally to arrangements and methods for suturing soft tissue to bone, and more particularly, to a system wherein soft tissue is sutured to a suture anchor, and a bone anchor is embedded in a bone, the suture anchor and the bone anchor then being mechanically coupled to one another in a manner whereby the engagement is reversible.

2. Description of the Related Art

The fixation of soft tissue to bone remains a perplexing problem. The physical properties of bone and soft tissue are so different that techniques which provide adequate fixation to bone do not provide adequate fixation to soft tissue. This problem is especially difficult when trying to use arthroscopic or mini incision techniques. The prior art has thrust at this problem with a variety of anchors which can couple suture material to bone. However, no system is known to be available which achieves adequate fixation of the soft tissue to bone.

Rotator cuff avulsions, rotator cuff tears close to the bone, and other soft tissue avulsions and tears are lesions consisting of separations of soft tissue from bone or near bone. A surgeon endeavoring to effect repair must adequately secure the torn soft tissue to the bone utilizing open surgical procedures. However, the repair cannot be achieved using current arthroscopic surgical techniques. The problems associated with known fixation devices, whether used arthroscopically or in standard surgical techniques, can be divided into three separate problems:

(1) soft cancellous bone and very hard cortical bone are not amenable to current surgical soft tissue to bone fixation devices. Known devices are suitable for the fixation of a soft tissue to average bone of average density;

(2) various sizes and configurations are required depending upon the sizes of the soft tissue and bone defects. Known arrangements, however, do not have any flexibility with regard to size or configuration; and (3) known arrangements do not permit the use of appropriate surgical techniques to maximize the soft tissue to bone fixation, to achieve adequate strength of the fixation.

One known arrangement for use in the fixation of soft tissue to bone employs two to four prongs. The prongs are embedded into the bone after pre-drilling a hole in the bone and preparing the bone surface to accept the soft tissue. The prongs are embedded in cancellous bone which is soft and can yield under stress.

The required preparation of the bone immediately above the device weakens the bone, thereby predisposing the bone to failure. Bone which is very narrow or very hard is difficult to prepare to accept this known device. There is no variation of the device for very soft cancellous bone. One attempt to overcome the difficulties associated with this known device require the use of double rows of the device in order to achieve adequate fixation to soft bone. This procedure is cumbersome and requires a large surgical exposure.

In the use of this known device, the force with which the soft tissue is drawn toward the bone is related to the tension placed on the suture during knot tying. However, when arthroscopic techniques are employed, the tension which is applied by the surgeon during knot tying is variable and inconsistent.

Another problem which is associated with the use of the known device occurs if the suture breaks after the device is embedded into bone. New suture material cannot be threaded through the device. Once the device is embedded in bone, there is no method of removing the device. The only way to salvage a broken suture is to place another device next to the one that has failed. The existence of extra metal embedded in bone is prone to infection. Additionally, the placement of multiple devices next to one another weakens the bone. Of course, since the device cannot easily be removed, its presence will complicate further reconstructive procedures.

Another known device for use in anchoring soft tissue to bone employs screw threads for bone fixation. This known device achieves an advantage over that described hereinabove in that it can be removed if the suture breaks during tightening. However, in all other respects the mechanics of this fixation device are similar to that described above, particularly in regard of tying and tensioning of the suture and soft tissue.

There currently are two absorbable fixation devices on the market. These devices penetrate the tissue directly, but do not use sutures. Tissue is tensioned using instruments while the device is driven through the soft tissue into a pre-drilled bone hole. Once the device is placed, there is no method of salvage. Thus, if the device fails, such as by fracturing, it cannot be removed from the bone.

All of the known devices transmit forces parallel to the direction of penetration into the bone. The pull-out strength of the fixation of the soft tissue to the bone is therefore directly related to the pull-out strength of the bone fixation device. In addition, all of the known devices secure the soft tissue directly to the bone above the fixation device. Any preparation of the bone to allow better healing of soft tissue to the bone weakens the bone in the area of the fixation device.

In addition to the foregoing, all of the known devices ignore the forces of the tendon during active contraction of the muscle attached to the tendon. Tension wire fixation techniques allow contraction of the muscles pulling on the fracture or soft tissue to compress the fractured bone or torn surfaces together, promoting healing. The current devices used to fix soft tissue to bone, allow the forces associated with contraction of the muscle attached to the soft tissue to distract the soft tissue away from the bone, thereby interfering with healing.

Current measurements of the efficacy of the state of the art soft tissue to bone fixation arrangements generally relate to the pull-out strength of the fixation devices or the strength and failure of the fixation to soft tissue. The actual strength of fixation is related to the strength of the entire complex, consisting of the soft tissue fixation, the fixation device, and the underlying bone.

When multiple fixation devices are used, problems with surgical techniques occur. All of the known surgical devices, such as those described herein, require that the device be placed in the bone with its sutures attached. If four such devices are used, eight sutures will be hanging in the surgical field attached to the bone, but not attached to soft tissue.

Once the surgeon places the sutures through the tendon, he has no way of applying tension on the sutures to see how well the soft tissue will be fixed to the bone. Once the sutures are placed in the soft tissue, it is difficult to replace them, in the event the placement is incorrect. Additionally, as previously stated, knot tying is difficult when attempting arthroscopic procedures. This compounds the problem of multiple free sutures in the joint.

In cancellous bone, the conventional tacks, screws, and staples do not provide adequate fixation to the bone. The bone is generally very soft and does not hold fixation devices well. There are available cancellous screws for use in fixing soft tissue to cancellous bone. These screws can be fitted with special washers for holding tendons and other soft tissue. The cancellous screws, however, stand proud above the bone and impinge against other bony structures in the joint or against other anatomic structures. Thus, there is a need for an arrangement which achieves a substantially flush fixation with respect to the surface of the bone.

It is, therefore, an object of this invention to provide a simple and economical device which removably fixes soft tissue to bone.

It is another object of this invention to provide an arrangement for anchoring soft tissue to soft cancellous bone, or very hard conical bone.

It is also an object of this invention to provide an arrangement for fixing soft tissue to bone which can be configured in a variety of sizes depending upon the size of the soft tissue and bone defects.

It is a further object of this invention to provide a system and method of tissue to bone fixation which permits proper surgical techniques to be employed to maximize the strength of the tissue to bone fixation.

It is additionally an object of this invention to provide a system of fixing a soft tissue to bone which does not require a large surgical exposure.

It is yet a further object of this invention to provide a system for fixing soft tissue to bone wherein the strength of the fixation does not rely upon the variable and inconsistent tension which is applied by a surgeon during the tying of a knot.

It is also another object of this invention to provide an apparatus and method of fixing soft tissue to bone which does not require the installation of a second bone anchor in the event a suture material breaks.

It is yet an additional object of this invention to provide an arrangement for fixing soft tissue to bone which does not require numerous sutures to hang in the surgical field.

It is still another object of this invention to provide a tissue to bone fixation arrangement which can be installed to be flush with the surface of the bone, or slightly therebelow.

SUMMARY OF THE INVENTION

The foregoing and other objects are achieved by this invention which provides, in a first apparatus aspect thereof, an arrangement for coupling soft tissue and bone of a living being. In accordance with the invention, the arrangement is provided with a suture anchor having a first coupling portion for coupling with the soil tissue of the living being, and a second coupling portion. A bone anchor is additionally provided, having an external portion for engaging with the bone of a living being, and an internal portion for engaging with the second coupling portion of the suture anchor.

In a highly advantageous embodiment of the invention, the second coupling portion of the suture anchor is provided with a resilient engagement element which applies a resilient biasing force against the internal portion of the bone anchor. The resilient engagement element may be provided with an extraction arrangement which facilitates the application of a force which is counter to the resilient biasing force. Thus, the suture anchor and the bone anchor can readily be disengaged.

In one embodiment the invention, the internal portion of the bone anchor has a rectangular cross-sectional configuration. However, in other embodiments, the internal portion of the bone anchor can have a round cross-sectional configuration.

In a highly advantageous embodiment of the invention, the second coupling portion of the suture anchor is provided with a coupling body for entering into the internal portion of the bone anchor. The resilient engagement element is in the form of a prong which is resiliently coupled to the coupling body of the suture anchor. In this embodiment, the prong has a predetermined surface contour, and the internal portion of the bone anchor has a correspondingly mating surface contour, the surface contours being adapted to interengage with one another. In one embodiment, the interengagement between the two surface contours is achieved in a step-wise manner as the suture anchor is urged into communication with the internal portion of the bone anchor. In a still further embodiment, the interengagement is achieved in a ratchet-like manner wherein the force required to pull the suture anchor from the bone anchor exceeds the force required to achieve the engagement.

In a still further embodiment of the invention, the second coupling portion has external threads formed thereon, and the internal portion of the bone anchor has internal threads formed therein. In this manner, the interengagement between the internal portion of the bone anchor and the second coupling portion of the suture anchor is achieved by threaded engagement between the external and internal threads. With respect to the suture anchor, the external threads of the second coupling portion may be formed on the prong which is resilient coupled to the coupling body.

The first coupling portion of the suture anchor is provided with a suture engagement portion which securely engages a suture material. In one embodiment, the suture engagement portion is provided with a first aperture for accommodating the suture material. In a further embodiment, the suture engagement portion is arranged to cooperate with the internal portion of the bone anchor to achieve a secure engagement with the suture material. The secure engagement is achieved by an interference fit with the suture material interposed between the suture anchor and the bone anchor. The interference fit may be facilitated by configuring the suture anchor to have a tapered configuration.

The external portion of the bone anchor has a round cross-sectional configuration and is provided with a screw thread formed thereon for engaging with the bone of the living being. The screw thread has predetermined pitch and depth characteristic which are determined in response to the type of bone of the living being into which the bone anchor means is intended to be installed. In addition, the bone anchor may be provided with an anchor tool engagement portion for engaging a bone anchor installation tool which will facilitate the application of a rotative force to the bone anchor during installation thereof. The engagement portion may be configured as a slot for a screwdriver, a hex-shaped aperture for a hex drive, or any of several known drive tool configurations.

In accordance with a further apparatus aspect of the invention, an arrangement for coupling soft tissue and bone of a living being is provided with a suture anchor having a first coupling portion for coupling with the soft tissue of the living being, and a second coupling portion, the second coupling portion having a predetermined coupling portion surface contour. The first coupling portion is adapted to engage a suture material for effecting the coupling between the first coupling portion and the soft tissue of the living being. There is additionally provided a bone anchor having an internal portion for engaging with the bone of the living being. The bone anchor has an internal portion which engages with the second coupling portion of the suture anchor. The internal portion of the bone anchor has a predetermined internal portion surface contour for engaging with the coupling portion surface contour. The suture anchor therefore is made to be removably engaged with the bone anchor.

In one embodiment of this further apparatus aspect of the invention, the suture anchor and the bone anchor are arranged to cooperate to apply a friction force to the suture material for securing same.

The second coupling portion of the suture anchor means may be formed as a prong having an outer surface on which is provided the predetermined coupling portion surface contour. A coupling body having first and second ends is coupled at the first end of the suture anchor. A resilient coupler resiliently couples the prong and the second end of the coupling body. In a preferred embodiment of the invention, the predetermined coupling portion surface contour and the predetermined internal portion surface contour constitute respective portions of interengageable outer and inner screw threads.

In accordance with a method aspect of the invention, the method includes the following steps:

coupling the soft tissue of the living being to a first coupling portion of a suture anchor;

coupling an external portion of a bone anchor with the bone of the living being; and engaging a second coupling portion of the suture anchor with an internal portion of the bone anchor.

In a preferred embodiment, the step of engaging includes the interengagement of the surface contours of the second coupling portion of the suture anchor with the internal portion of the bone anchor. This interengagement is reversible, whereby the suture anchor and the bone anchor can be readily disengaged.

In accordance with a further embodiment of the method aspect of the invention, the step of coupling the soft tissue of the living being includes the further step of applying a suture material to effect the coupling of the soft tissue to the first coupling portion of the suture anchor. The suture material is threaded through a passageway in the first coupling portion of the suture anchor. In one highly advantageous embodiment of the invention, a force is applied to the suture material by compressing same between the suture anchor and the bone anchor, thereby enhancing, with the use of friction, the security of the engagement of the suture material with the suture and bone anchors. Of course, the suture can easily be removed by disengaging the suture anchor from the bone anchor.

BRIEF DESCRIPTION OF THE DRAWING

Comprehension of the invention is facilitated by reading the following detailed description, in conjunction with the annexed drawing, in which:

FIG. 14 is a schematic representation of a specific embodiment of the invention having an hexagonal drive configuration;

FIGS. 17 and 18 are schematic representations of respective bone and soft tissue anchors which do not employ apertures to accept the suture material (not shown), and instead these sutures are anchored by friction between the bone anchor and the soft tissue anchor;

DETAILED DESCRIPTION

Figure 1:
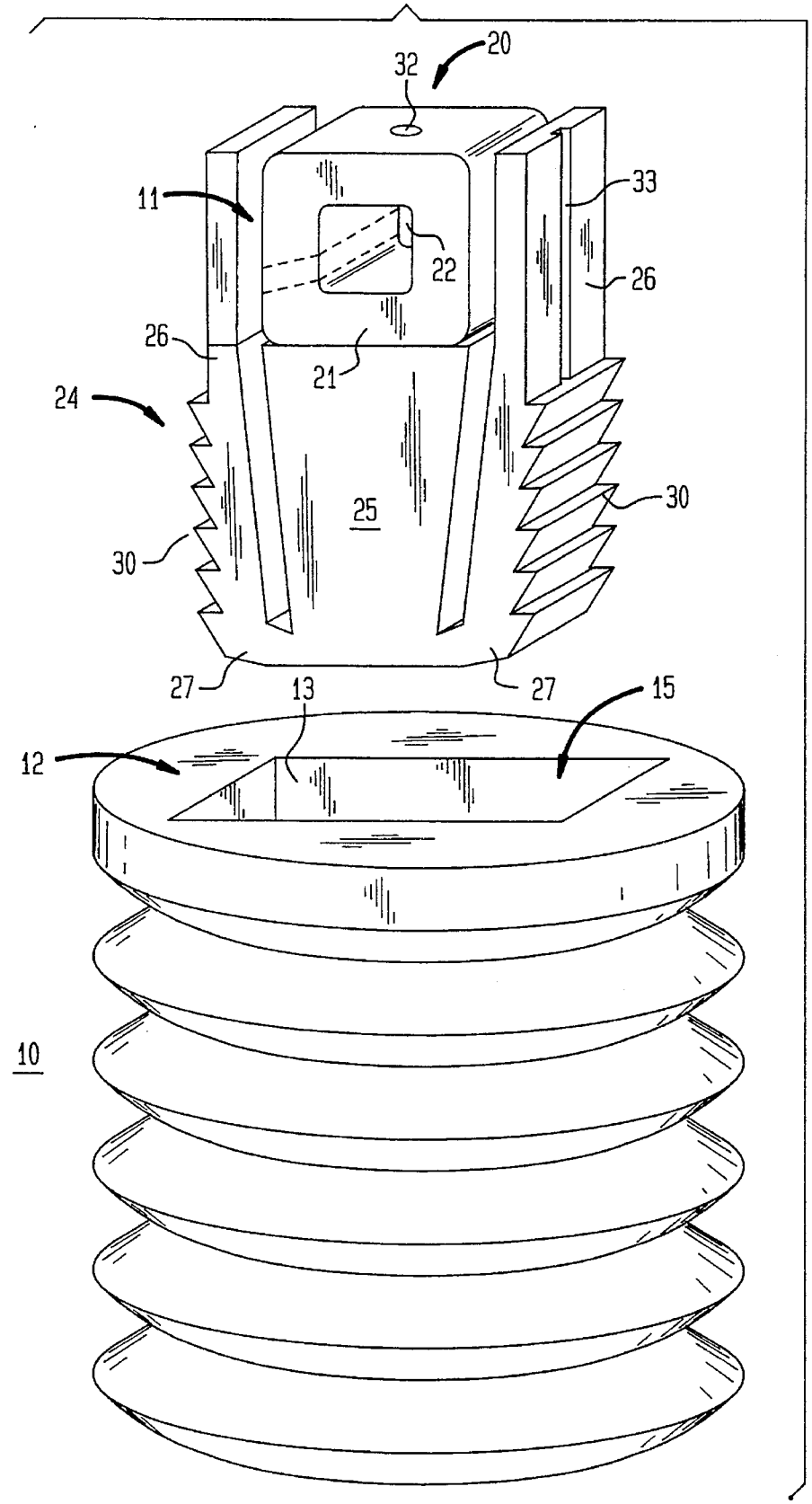
FIG. 1 is an isometric representation of a specific illustrative embodiment of the invention showing a suture anchor disengaged from a bone anchor.

FIG. 1 is an isometric representation of a specific illustrative embodiment of the invention 10 showing a suture anchor, generally designated as 11 and a bone anchor, generally designated as 12. Bone anchor 12 is designed to give maximum fixation to bone (not shown in this figure). The length, diameter, and configuration of bone anchor 12 are matched to the type of bone encountered during the surgical procedure. Bone anchor 12 is not attached to any suture material (not shown) and its placement is independent of suture placement. In use, the surgeon determines the best place for the bone anchor without concern over the suture material. The length of the anchor will depend on the length needed to provide maximum bone fixation. Bone anchor 12 is designed to accept a modified screw driver system and to accommodate suture anchor 11, in rectangular aperture 13. The bone anchor is screwed into a pre-drilled hole in the bone (not shown). The size of the threads and diameter of the bone anchor are predetermined to accommodate different bone densities and different anatomical sites.

Suture anchor 11 is designed to accept a suture material (not shown) and to lock into an internal portion 15 of the bone anchor. As shown, internal portion 15 of the bone anchor is accessed via rectangular aperture 13, of this specific embodiment. The suture anchor can be very large or very small depending on the size of the bone anchor and the size of the soft tissue fixation area (not shown).

In use, sutures (not shown) are placed into the soft tissue using either standard or arthroscopic techniques. Placement of the suture is determined by estimating the best position of the suture material within the tissue, in the judgment of the surgeon. Since the suture material is not attached to the bone anchor at this point, the suture can easily be removed and replaced if the position of the suture is not optimal. The surgeon can then apply tension on the sutures to determine whether suture placement in the soft tissue is optimal. Once the surgeon is satisfied with the suture placement in the soft tissue, the surgeon can then thread the suture through the apertures in the suture anchor and then commence attachment of the suture anchor to the bone anchor. In this specific illustrative embodiment of the invention, suture anchor 11 has a first coupling portion 20 having a suture engagement portion 21. Suture engagement portion 21 has a first aperture 22 through which the suture material (not shown) is threaded. First coupling portion 20 is arranged adjacent to a second coupling portion 24 which has a coupling body 25 and, in this embodiment, a pair of prongs 26 which are resiliently coupled to the coupling body via resilient coupling elements 27.

In this specific illustrative embodiment of the invention, prongs 26 are provided on their exterior surfaces with a plurality of steps 30 which form a predetermined outer surface contour of the prongs. During insertion of the suture anchor into the internal portion of bone anchor 12, steps 30 interengage with correspondingly configured steps (not shown) in internal portion 15 of the bone anchor. Thus, internal portion 15 of the bone anchor has a surface contour which interengages with the outer surface contour of the suture anchor.

In this arrangement, as the suture anchor is urged into engagement with the internal portion of bone anchor 12, there are provided multiple locking positions as the respective surface contours interengage with one another. It is a preferred characteristic of this invention that in the first locking position, the suture anchor becomes firmly locked into the bone anchor without impeding the ability of the surgeon to apply tension to a suture (not shown) which has been attached to the soft tissue (not shown) and threaded through first aperture 22 of suture engagement portion 21.

The final locking position, which is achieved when the suture anchor is fully engaged in the bone anchor, firmly fixes the suture material (not shown) by friction between suture anchor 11 and the internal surface of bone anchor 12. This friction interference fit provides security to the fixation of the soft tissue beyond any knots applied to the suture by the surgeon. Persons of skill in the art can configure the dimensions of the suture anchor, with respect to the dimensions of the internal portion of bone anchor 12, to insure maximum friction with the suture material, which may be of varying diameters and fiber construction.

FIG. 1 additionally shows a hole 32 on a top surface of first coupling portion 20 of the suture anchor. This hole may be used to accommodate a driving pin (not shown), and may be shaped to receive a driver tool (not shown), such as an hexagonal wrench, a cross-blade screw driver, or a slotted screw driver.

The configuration of the interface between the suture anchor and the bone anchor is designed to permit insertion of the suture anchor into the bone anchor in response to the application of a direct pressure forcing the suture anchor into the bone anchor. At the time of insertion, the suture material (not shown) is attached to the suture anchor, and therefore, rotation to advance a threaded system cannot be used. Only direct (downward in the drawing) pressure is used.

The interface of the respective surface contours, in this embodiment of the invention, is designed to allow removal of the suture anchor if the surgeon believes that the suture material has not been placed in the correct position. As will be described herein, the fixation device is configured so that the suture anchor can be disengaged from the bone anchor either by applying a pressure counter to that exerted by prongs 26, or in other embodiments, to unscrew the suture anchor from the bone anchor.

In the embodiment of FIG. 1, suture anchor 11 is disengaged from bone anchor 12 by application of a laterally inward force to prongs 26. As will be described hereinbelow, prongs 26 are provided with respective notches 33 which facilitate engagement of a removal tool (not shown).

Figure 2:
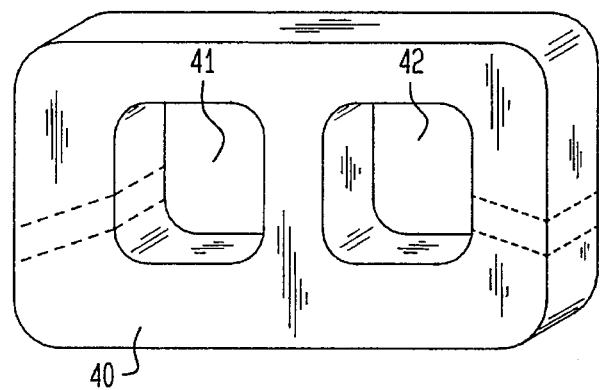
FIG. 2 is a representation of a first coupling portion of a suture anchor having a pair of apertures for engaging the suture material.

FIG. 2 is a plan view of a first coupling portion 40 which may be used in place of first coupling portion 20 shown in FIG. 1. The first coupling portion in FIG. 2 is shown to have a pair of apertures 41 and 42 through which the suture material (not shown) can be threaded.

Figure 3:
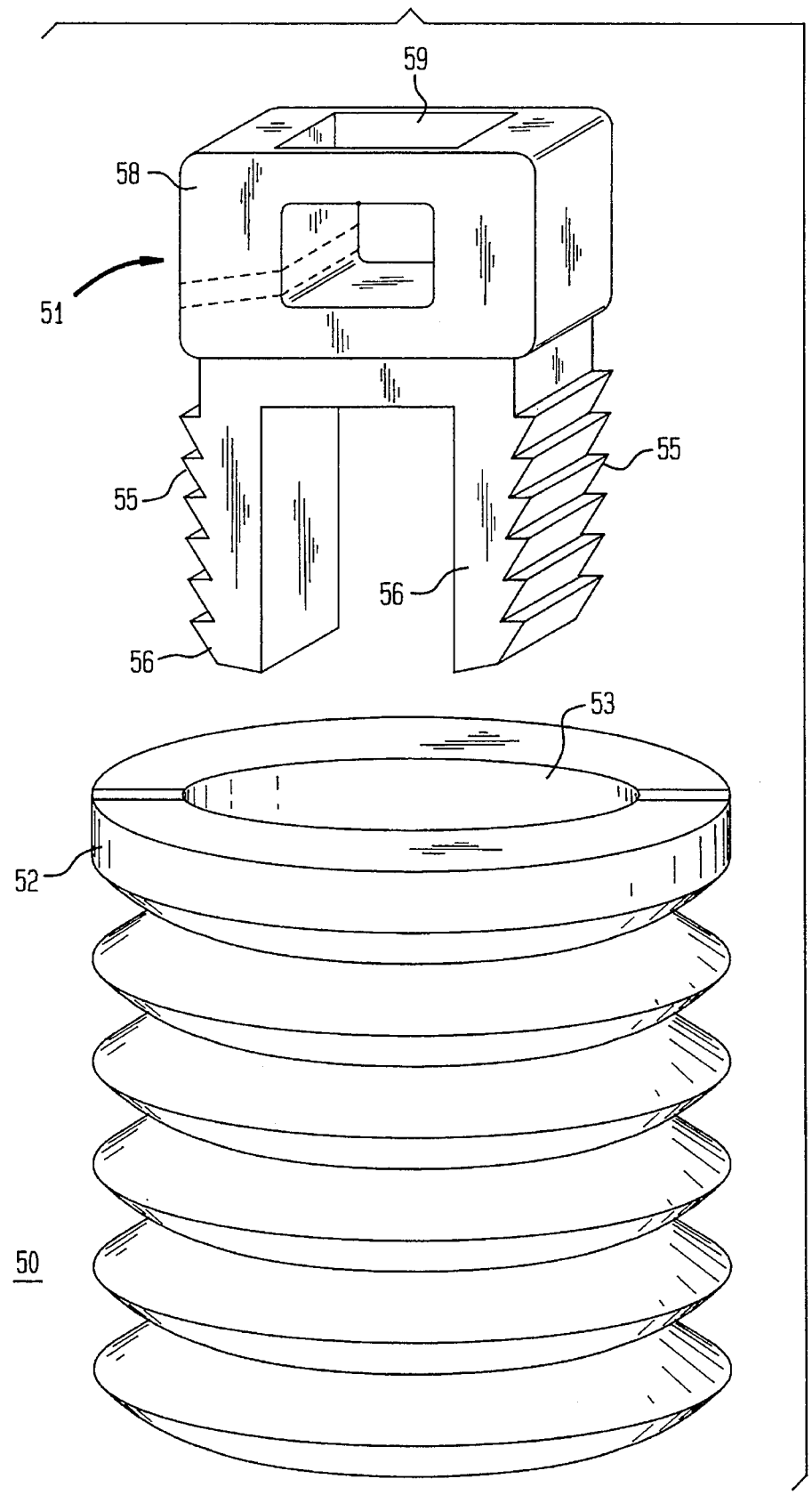
FIG. 3 is an isometric representation of an embodiment of the invention wherein the suture anchor can be threadedly engaged with the internal portion of the bone anchor.

FIG. 3 is an isometric representation of fixation device 50 having a suture anchor 51 and a bone anchor 52. In this embodiment of the invention, internal portion 53 of bone anchor 52 has a round cross-sectional configuration. The suture anchor has a predetermined surface contour 55 on prongs 56 which extend, in this embodiment, away from first coupling portion 58 of the suture anchor. The surface contour on the prongs corresponds to a screw thread which interengages with a corresponding surface contour (not shown) in internal portion 53 of the bone anchor. In this specific embodiment, the first coupling portion is provided with a slot 59 for engaging a driver tool (not shown), such as a screw driver.

The configuration of fixation device 50 is such that the application of a direct (downward) force will drive the suture anchor into the bone anchor. If the suture anchor must be removed, counterclockwise rotation of the suture anchor will cause it to back out of the bone anchor. Thus, no rotation of the suture anchor is required to achieve the initial engagement but a tool may be required to effect disengagement. The orientation of the engagement of the suture anchor and the bone anchor allows the suture anchor to be unscrewed if the position of the soft tissue fixation (not shown) is determined by the surgeon to be poor. In other embodiments of the invention, the suture anchor is not limited to two prongs 56. One or more threaded prongs, such as prongs 56, may be employed in the practice of the invention.

In the event that the surgeon believes that the suture anchor was not in proper position, the suture (not shown) would be cut, thereby allowing the suture anchor to be rotated. The suture anchor would then be unscrewed from the bone anchor, and new sutures would be created.

The configuration of the interface between the bone anchor and the suture anchor may be constructed in certain embodiments to allow only partial release. The two units would be connected in such a manner that a partial release would allow the suture to be removed from the anchor without disruption of the anchor. A new suture may then be threaded through the eye of the anchor. At no time would the surgeon have to remove the entire anchoring system from the bone in order to change the suture.

Figure 4:
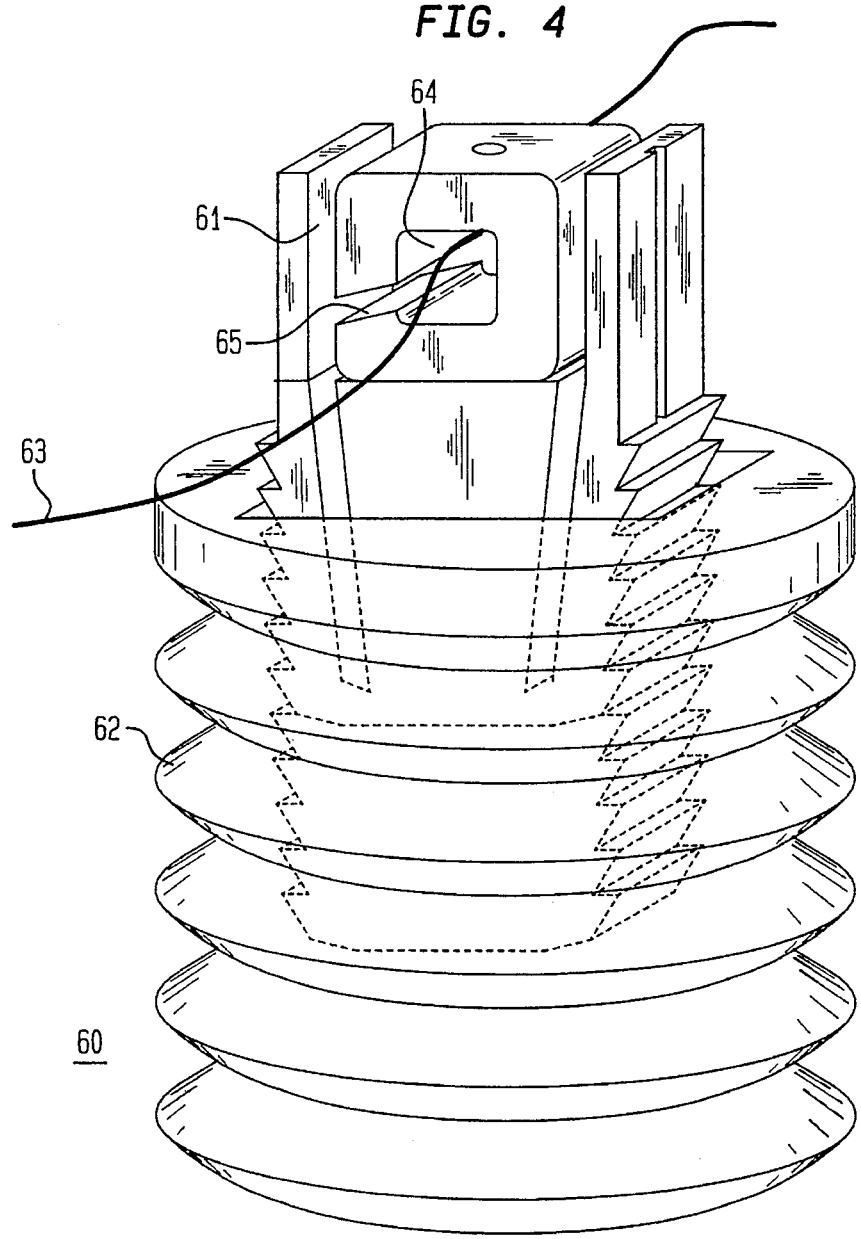
FIG. 4 is a partially cross-sectional isometric representation of an embodiment of the invention illustrating the suture anchor partially engaged with the bone anchor, and further showing a suture material.

FIG. 4 is an isometric representation of a fixation device 60 showing a suture anchor 61 in partial engagement with a bone anchor 62. A suture material 63 is shown to be threaded through aperture 64 in the suture anchor.

When the suture material is threaded through the suture anchor, an attempt to screw the suture anchor into the bone anchor would wind or twist the suture material. In order to avoid this situation, the suture anchor has prongs which will resiliently yield sufficiently to allow the suture anchor to be driven into the threaded portion of the bone anchor by direct pressure, as previously described. The configuration of the threads on the suture anchor is such that it will allow it to be driven by direct pressure without damage to the threads. Once locked in place, the threads are designed to resist pressure that would tend to pull the suture anchor out of the bone anchor. Driven partially in, as shown, a suture material can easily be threaded through aperture 64, or under a optional slot 65, which in this specific illustrative embodiment of the invention is shown in phantom. Once engaged, the surgeon can pull on the suture material while it is threaded through the suture anchor and apply a proper tension to the suture to adjust the position of the soft tissue (not shown) and the tension of the suture thereon.

Figure 5:
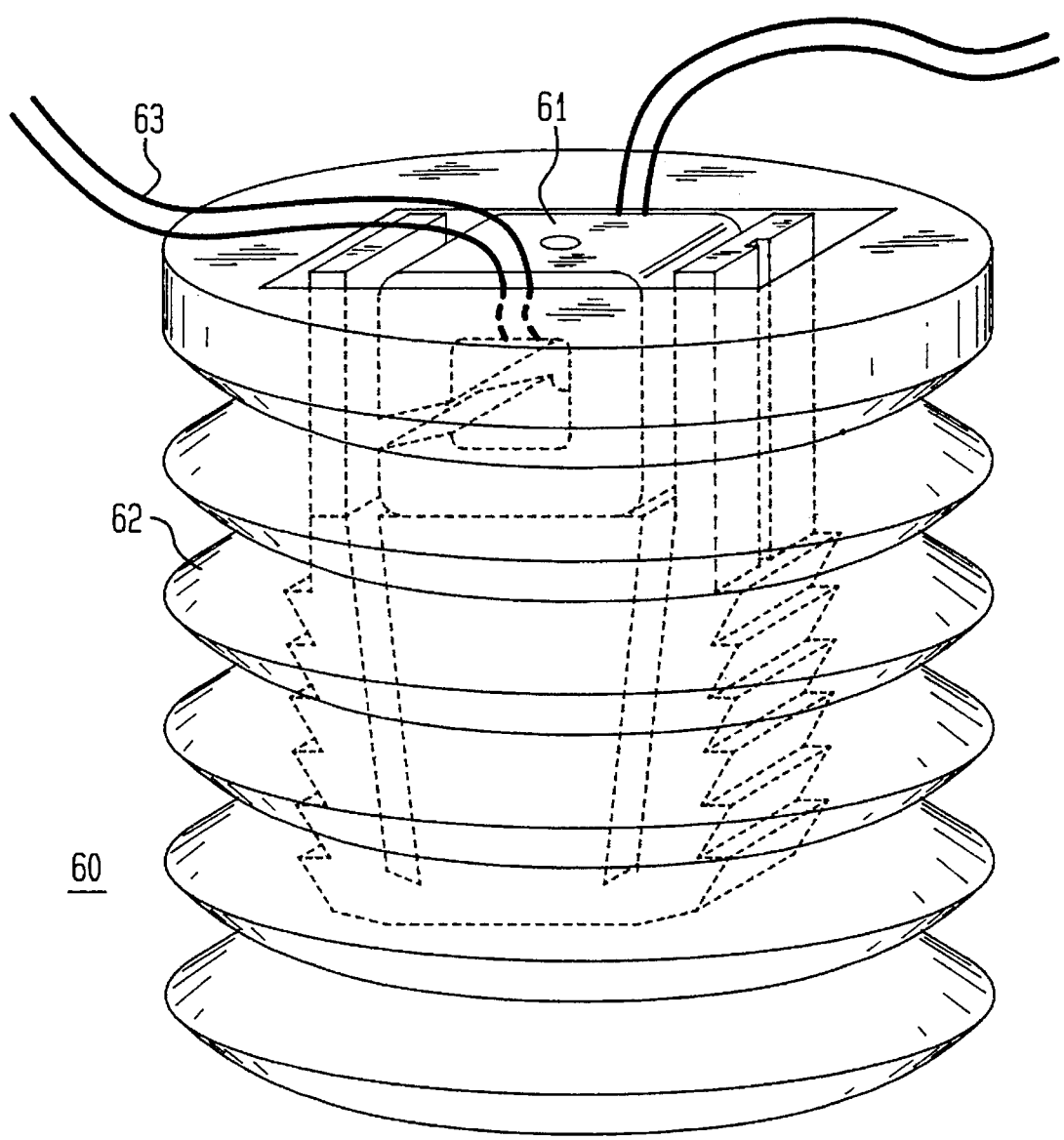
FIG. 5 is a isometric representation of an embodiment of the invention showing the suture anchor fully engaged within the bone anchor.

FIG. 5 is an isometric representation of the embodiment of FIG. 4 wherein suture anchor 61 is shown to be fully engaged with bone anchor 62. Once the anchors are locked in place, sutures 63 are held by friction. Knots can be tied in the sutures to provide additional fixation.

Figure 6:
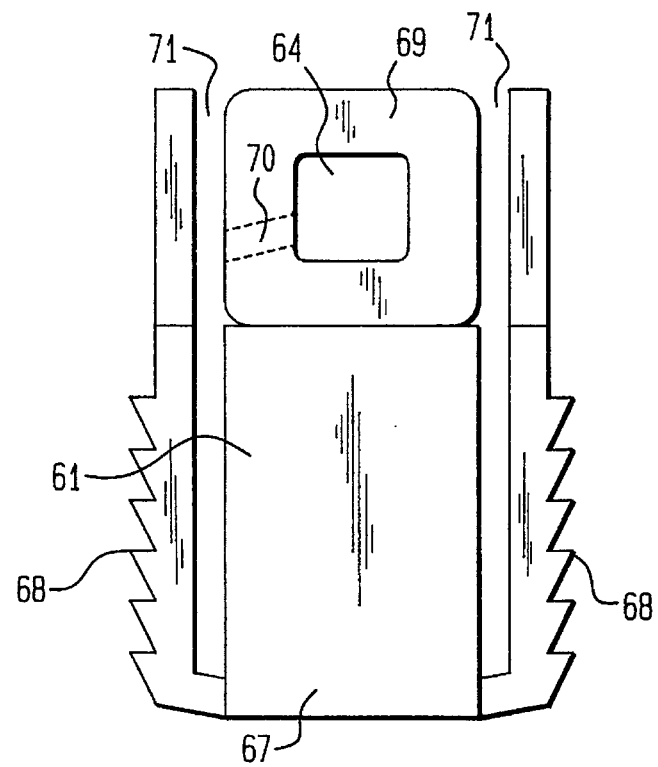
FIG. 6 is an elevational view of a suture anchor which is adapted to permit the suture material to be placed in the aperture of the suture anchor after there has been partial engagement between the suture anchor and the bone anchors.

FIG. 6 is an elevational view of suture anchor 61 which, as previously described, has a coupling body 67 with prongs, designated here as prongs 68, resiliently coupled thereto, and a respective first coupling portion 69 having an aperture 64 therethrough. In this embodiment, a slot 70 is placed in the suture anchor, as previously described. The suture material (not shown) may be placed through aperture 64 when the suture anchor is partially engaged with the bone anchor, as shown in FIG. 4. A slight slope in the upper end of the suture anchor allows for maximum pressure to be exerted on the suture material. There is additionally shown in the figure a space 71 between each of the prongs and the body of the suture anchor. Such spaces allow the prongs to be compressed laterally inwardly, reducing the effective cross-sectional area of the suture anchor, and thereby permitting same to be disengaged from the bone anchor for insertion or removal.

Figure 7:
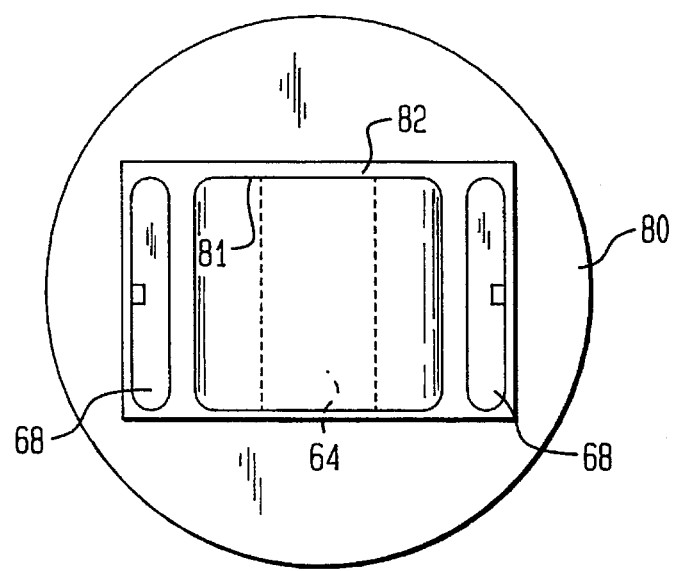
FIG. 7 is a plan representation which shows engagement between the suture and bone anchors.

FIG. 7 is a top plan view of suture anchor 61 inserted into a bone anchor 80 having a rectangular internal cross-section. In certain embodiments, the walls of the suture anchor may be sloped slightly to increase the frictional pressure which is applied to the suture material as engagement between the suture and bone anchors progresses. Preferably, the side walls of the suture anchor, such as side wall 81, is configured to be quite smooth to avoid damage to the suture material (not shown). The resulting clearance 82 is configured to be 50% or less of the diameter of the suture material (not shown) to effect firm frictional engagement.

Figure 8:
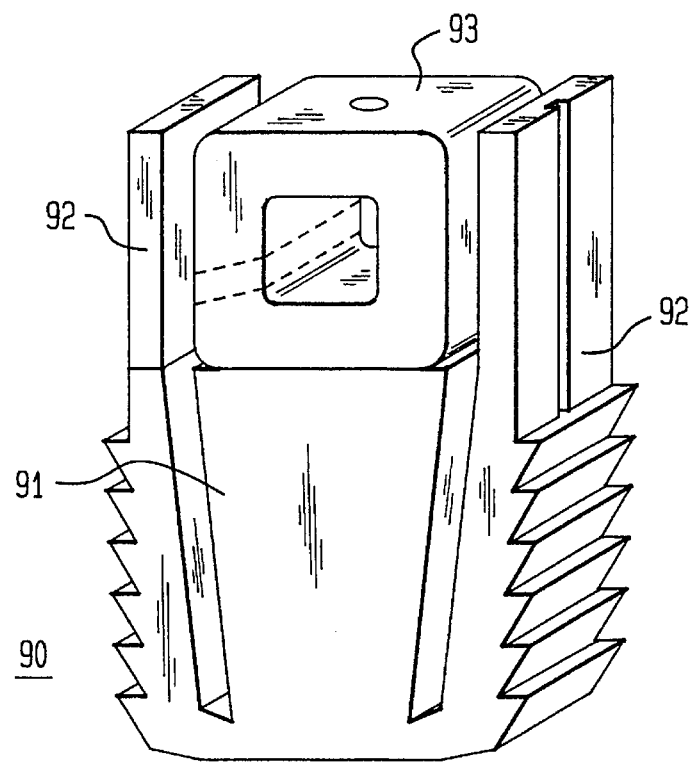
FIG. 8 is an isometric representation of another embodiment of a suture anchor.

FIG. 8 is an isometric representation of a specific embodiment of a suture anchor 90 which is shown to have a tapered configuration in its coupling body 91. In addition, the ends of prongs 92 may extend upward slightly beyond surface 93 of the suture anchor whereby disengagement of the suture anchor from the bone anchor, particularly in embodiments where surface 93 is arranged substantially flush with the upper end of the bone anchor, and the bone itself is facilitated.

Figure 9:
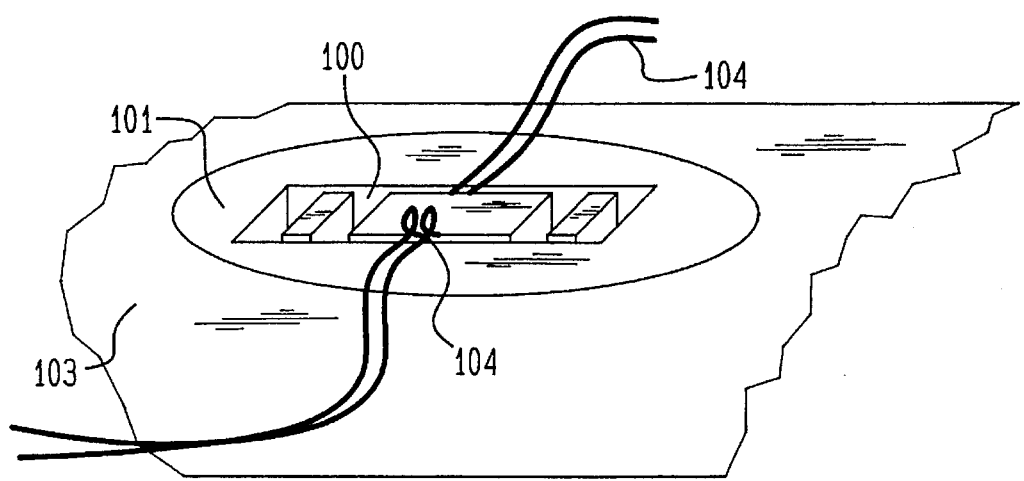
FIG. 9 is an isometric representation showing the bone and suture anchors installed to be flush with the surface of the bone, and further showing the suture material extending therefrom.

FIG. 9 illustrates a substantially flush arrangement of a suture anchor 100 fully inserted in a bone anchor 101, the bone anchor being installed in a surgical field of bone 103. As shown, suture material 104 is compressed between the side walls of the suture anchor and the internal walls of the bone anchor.

Figure 10:
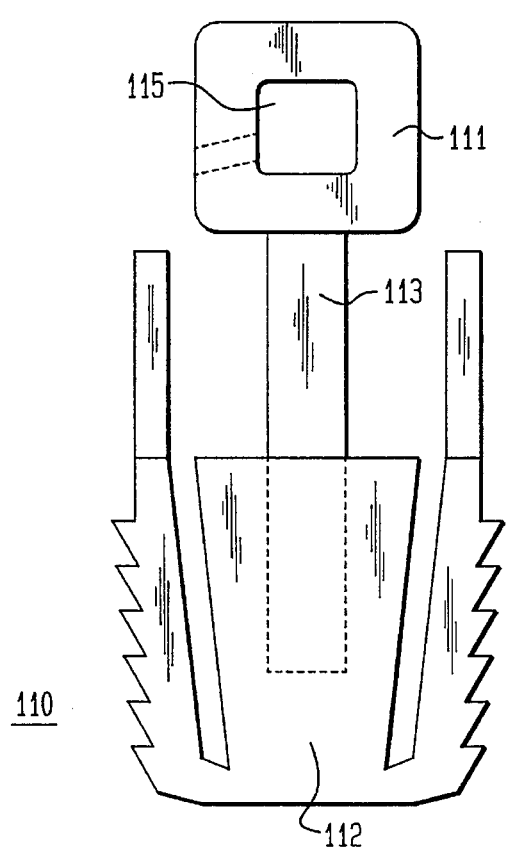
FIGS. 10 and 11 are elevational views which show an additional embodiment of a suture anchor wherein the suture material is wound on the suture anchor before final engagement into the bone anchor.
Figure 11:
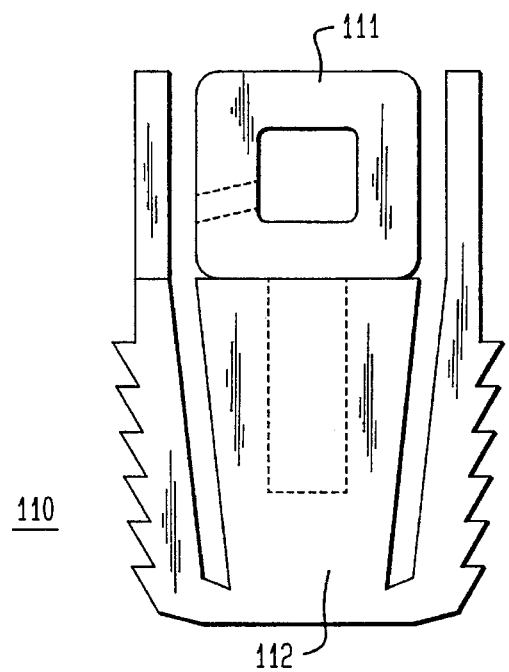

FIG. 10 is an elevational representation of a suture anchor 110 which is configured for special circumstances wherein a suture material (not shown) is wound around the suture anchor prior to final engagement with the bone anchor (not shown in this figure). In this embodiment, a first coupling portion 111 is axially displaceable from a coupling body 112 to produce an exposed coupling neck 113. While suture anchor 110 is partially engaged with its corresponding bone anchor (not shown), the suture material (not shown in this figure) is threaded through aperture 115 and then first coupling portion 111 is rotated to wind up the suture material for maximum tightness. Once the requisite tightness has been achieved, the first coupling portion is locked in place by further penetration into the bone anchor. FIG. 11 is an elevational view which illustrates suture anchor 110 after first coupling portion 111 has been engaged with coupling body 112.

Figure 12:
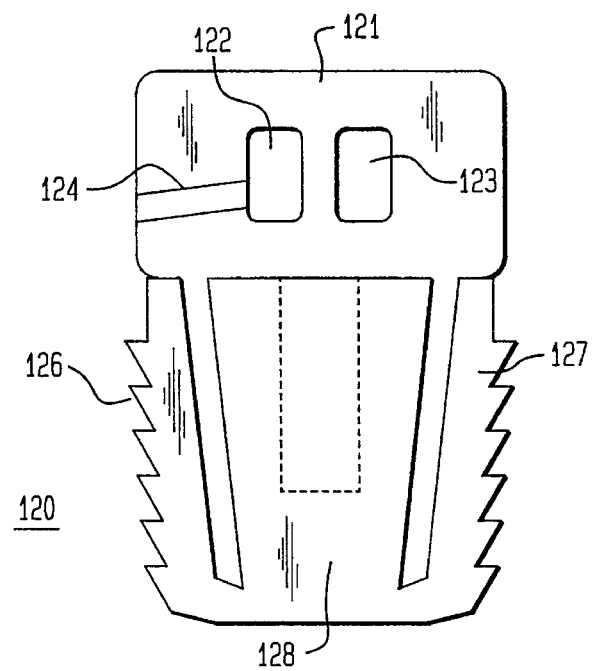
FIG. 12 is a plan view of a suture anchor embodiment wherein the prongs terminate below the suture coupling portion.

FIG. 12 is a plan view of a suture anchor 120 having a first coupling portion 121 with two apertures 122 and 123 therein. In addition, first coupling portion 121 is provided with a slot 124 for engaging the suture material (not shown in this figure) as previously described. In this embodiment, however, prongs 126 and 127 do not extend upward beyond the first coupling portion. The prongs, however, are resiliently coupled to coupling body 128, as previously described.

Figure 13:
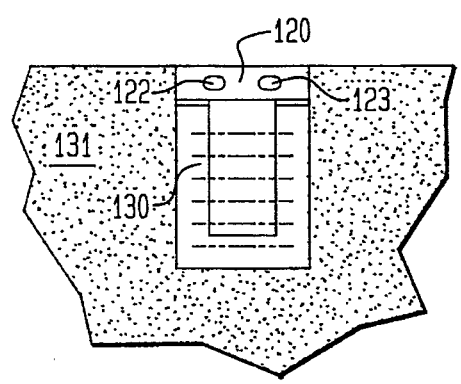
FIG. 13 is a schematic representation of the installation of the suture anchor of FIG. 12 wherein the bone anchor is driven below the surface of the bone and the suture material is not locked.

FIG. 13 is a schematic representation of suture anchor 120 engaged in a bone anchor 130 which has been installed in bone 131. As shown, bone anchor 130 is installed in the bone so as to be recessed therein, so that a substantially flush engagement is achieved at the bone surface when the suture anchor is installed. The installation the bone anchor below the surface of the bone provides maximum bone to soft tissue contact. The sutures would then be tied, prior to final engagement of the suture anchor to the bone anchor, creating a tight bone to soft tissue contact surface. As previously described, the suture material is threaded through apertures 122 and 123 prior to completing the engagement between the suture and bone anchors.

FIGS. 14 A and 14B together constitute a schematic representation of a fixation device 140 wherein an hexagonal indentation 141 is provided on the top surface of a suture anchor 142, shown in FIG. 14A, for facilitating installation of the suture anchor into a bone anchor. In this embodiment, internal side walls 145 of the bone anchor, shown in FIG. 14B, are sloped slightly inwardly to achieve a tighter grip on the suture material (not shown) as the suture anchor is driven into the bone anchor.

Figure 15:
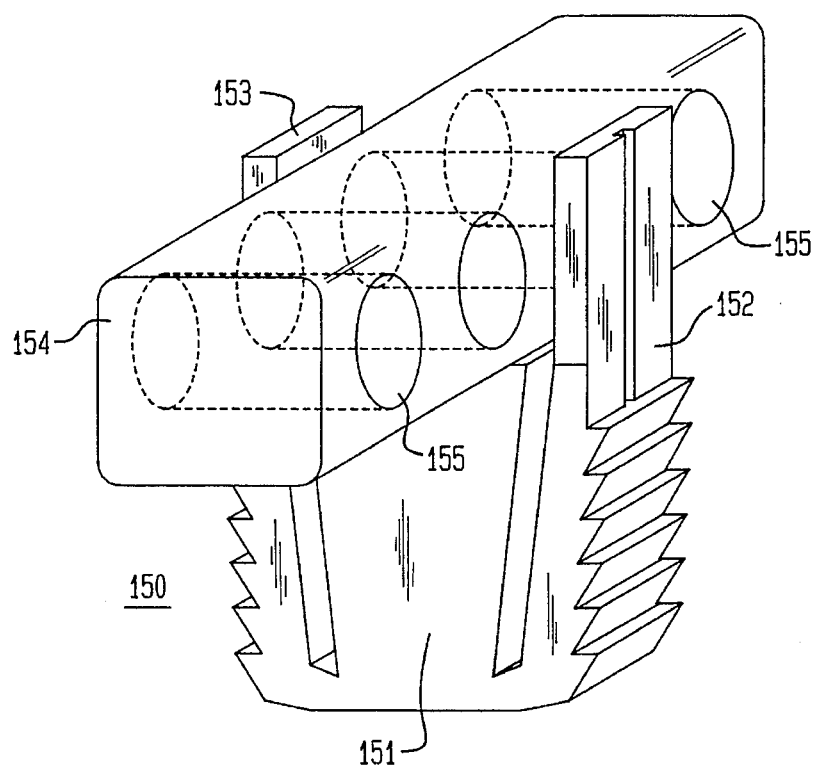
FIG. 15 is an isometric representation of a specific embodiment of a suture anchor wherein multiple apertures are used to attach a large area of soft tissue.

FIG. 15 is an isometric representation of a specific embodiment of the invention wherein multiple sutures can be placed on the same suture anchor. In this embodiment, suture anchor 150 has a coupling body 151 with resilient installed prongs 152 and 153, as previously described. A first coupling portion 154 is installed on the coupling body and is provided with a plurality of apertures 155 therethrough. This arrangement is particularly advantageous when attaching a large area of soft tissue to bone using only one bone anchor.

Figure 16:
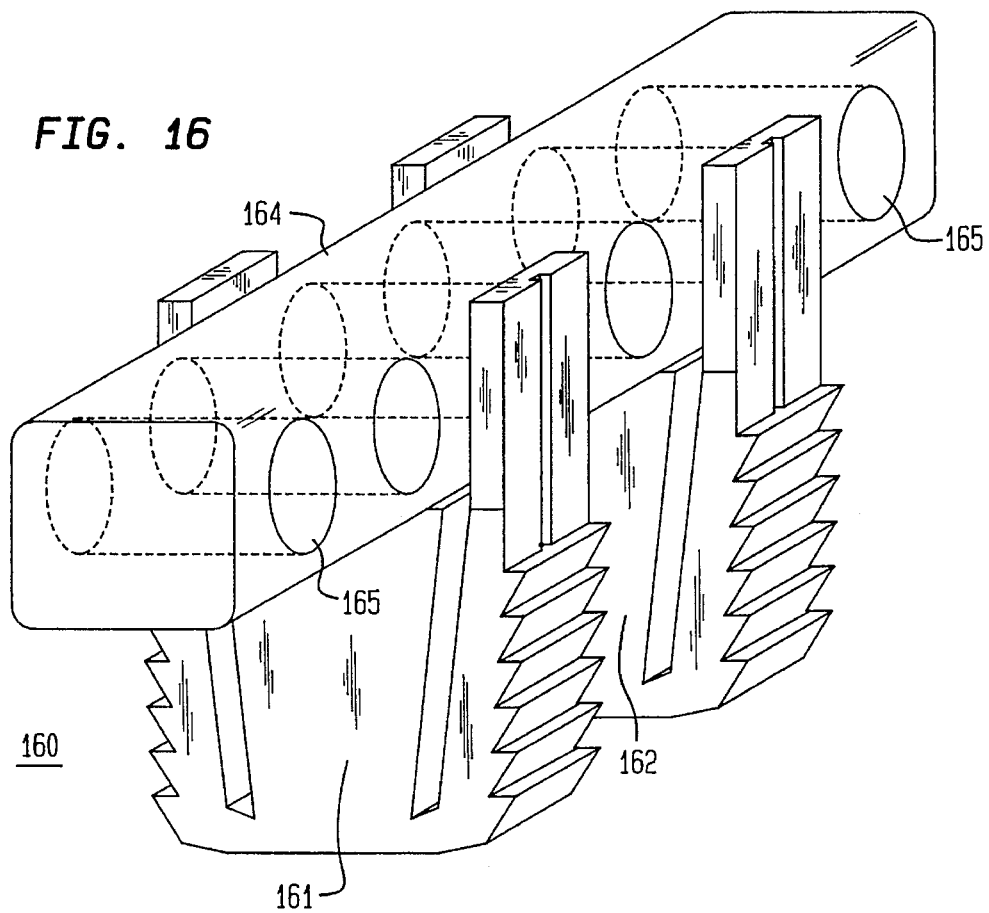
FIG. 16 is an isometric representation of a suture anchor arrangement similar to that shown in FIG. 15, wherein multiple suture anchors are employed.

FIG. 16 is a specific illustrative embodiment of a dual suture anchor 160. In this embodiment, suture anchors 161 and 162, each configured as previously described, are coupled to a common first coupling portion 164 which has a plurality of apertures 165 therethrough. This arrangement permits a large area of soft tissue to be attached to bone, and requires two bone anchors (not shown) to be employed.

The suture anchors of FIGS. 15 and 16 can be used to anchor a large area of soft tissue, as will be required in the repairing of large soft tissue defects. Persons of skill in the art can configure templates and jigs which would allow the placement of multiple bone anchors to accept the dual suture anchor embodiment of FIG. 16.

FIGS. 17 and 18 are simplified representations of embodiments of the invention which are useful when small bone fragments are to be attached to large bones, particularly when the larger bones are osteoporotic. Instead of using a suture anchor, as previously described, a screw 170 is used. The relatively thin shank of screw 170 will not weaken a small piece of bone (not shown). A larger diameter screw 171, which is shown schematically in this figure, functions as a bone anchor and is provided with larger threads to hold in a greater tuberosity. As such, screw 171 functions as a bone anchor, as previously described. In some embodiments of the invention, a soft washer (not shown) can be employed with the use of screw 170 when it is engaged with large diameter screw 171.

Figure 19:
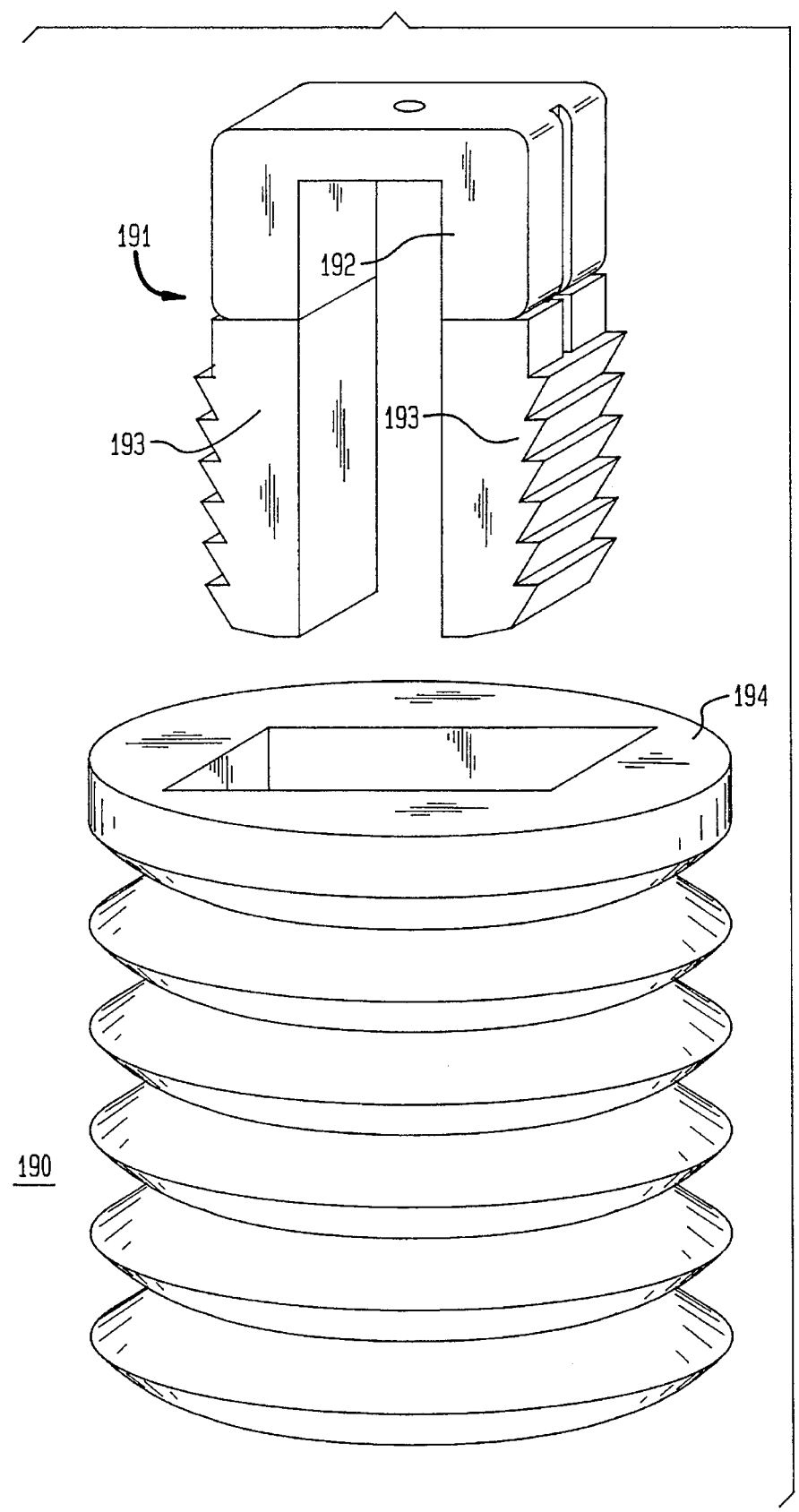
FIG. 19 is an isometric representation of an embodiment of the invention wherein a slot is provided to accept the suture material, and the suture material is anchored in place by friction.

FIG. 19 is an isometric representation of a still further embodiment of the invention. As shown, fixation device 190 employs a suture anchor 191 having a first coupling portion 192 with no apertures therethrough. In this embodiment, prongs 193 are engaged with bone anchor 194, and the suture material (not shown) is anchored in place by friction between the bone anchor and the suture anchor.

Figure 20:
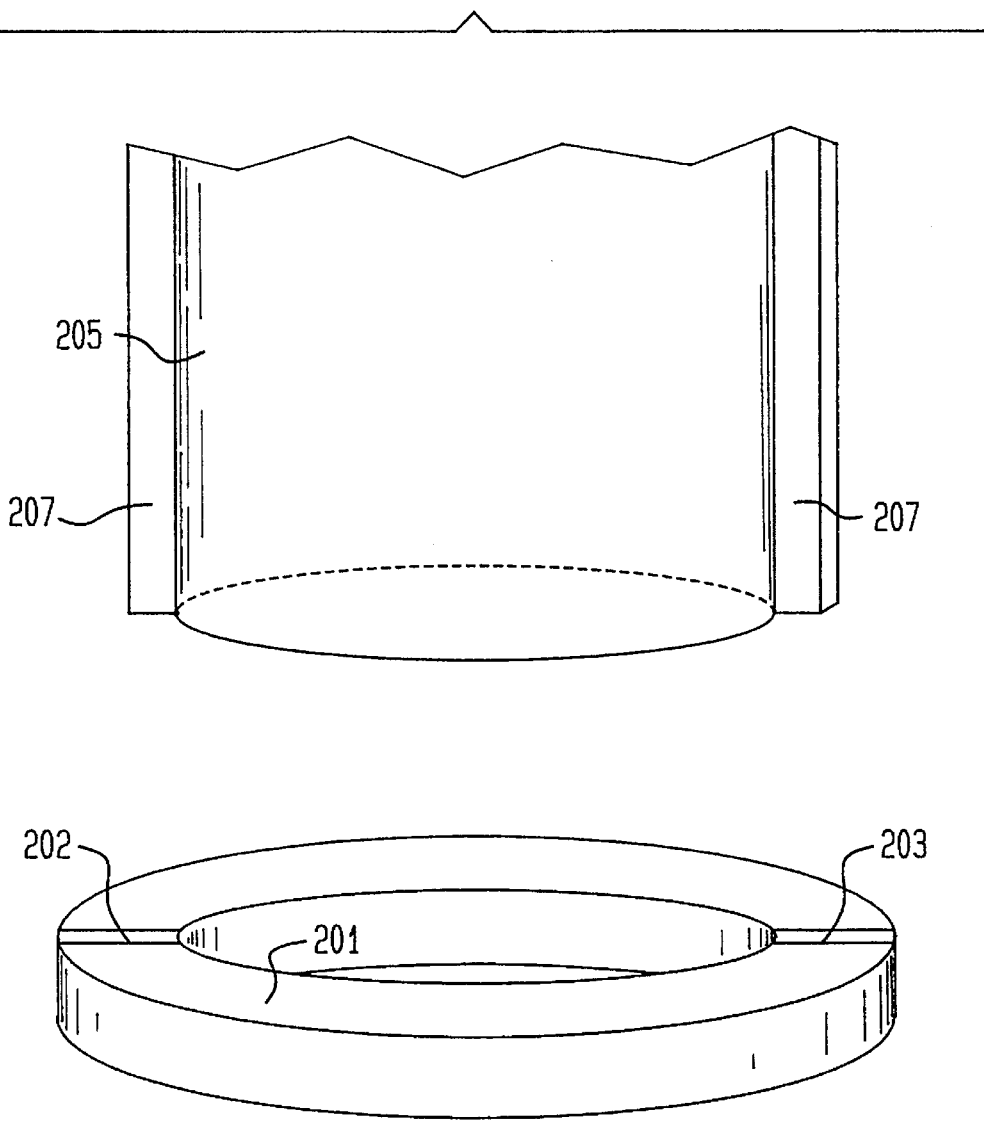
FIG. 20 is an isometric representation of an arrangement showing a special tool for driving the bone anchor rotatively into the bone.

FIG. 20 is an isometric representation of a bone anchor 201 having slots 202 and 203 arranged on its top surface. An installation tool 205 is provided with radial extension 207 and 208 which engage slots 202 and 203, respectively. Tool 205 therefore is useful to rotate bone anchor 201, in the form of a special screw driver, whereby the bone anchor is screwed into a pre-drilled hole in the bone (not shown), as previously described. In this embodiment, bone anchor 201 has a circular internal cross-section.

Although the invention has been described in terms of specific embodiments and applications, persons skilled in the an can, in light of this teaching, generate additional embodiments without exceeding the scope or departing from the spirit of the claimed invention. Accordingly, it is to be understood that the drawing and description in this disclosure are proffered to facilitate comprehension of the invention, and should not be construed to limit the scope thereof.

What is claimed is:

1. An arrangement for coupling soft tissue and bone of a living being, the arrangement comprising:

suture anchor means having a first coupling portion for coupling with the soft tissue of the living being, and a second coupling portion comprising resilient engagement means;

bone anchor means having an external portion for engaging with the bone of the living being, and an internal portion for engaging with said second coupling portion of said suture anchor means, whereby said resilient engagement means of said suture anchor means applies a resilient biasing force against said internal portion of said bone anchor means; and an extraction arrangement formed on said resilient engagement means for facilitating the application of a force counter to said resilient biasing force, thereby facilitating disengagement between said suture anchor means and said bone anchor means.

2. The arrangement of claim 1 wherein said internal portion of said bone anchor means has a rectangular cross-sectional configuration.

3. The arrangement of claim 1 wherein said internal portion of said bone anchor means has a round cross-sectional configuration.

4. The arrangement of claim 1 wherein said second coupling portion comprises a coupling body for entering into said internal portion of said bone anchor means, and said resilient engagement means comprises a prong which is resiliently coupled to said coupling body of said suture anchor means.

5. The arrangement of claim 4 wherein said prong has a predetermined surface contour and said internal portion of said bone anchor means has a correspondingly mating surface contour, said surface contours being adapted to interengage with one another.

6. The arrangement of claim 5 wherein said surface contour of said prong and said surface contour of said internal portion of said bone anchor means are adapted to interengage with one another in a sequential plurality of locking positions as said suture anchor means is urged into communication with said bone anchor means.

7. The arrangement of claim 6 wherein said surface contour of said prong and said surface contour of said internal portion of said bone anchor means are adapted to interengage with one another in a manner wherein the force required to pull said suture anchor means from said bone anchor means exceeds the force required to achieve the engagement.

8. The arrangement of claim 1 wherein said first coupling portion is provided with a suture engagement portion for securely engaging a suture material.

9. The arrangement of claim 8 wherein said suture engagement portion is provided with at least a first aperture for accommodating a suture material.

10. The arrangement of claim 9 wherein said suture engagement portion is arranged to cooperate with said internal portion of said bone anchor means for achieving a secure engagement with the suture material.

11. The arrangement of claim 10 wherein the suture material comprises a suture, said suture engagement portion and said internal portion of said bone anchor means being arranged to achieve an interference fit when said suture interposed is therebetween, whereby a friction force is applied to enhance the secure engagement with the suture material of said suture.

12. The arrangement of claim 11 wherein said internal portion of said bone anchor means has a tapered cross-sectional configuration for enhancing said interference fit.

13. The arrangement of claim 1 wherein said external portion of said bone anchor means has a round cross-sectional configuration and is provided with a screw thread formed thereon for engaging with the bone of the living being.

14. The arrangement of claim 13 wherein said screw thread formed on said external portion of said bone anchor means has predetermined pitch and depth characteristics which are determined in response to the type of bone of the living being into which said bone anchor means is intended to be installed.

15. The arrangement of claim 13 wherein said bone anchor means is further provided with bone anchor tool engagement means for engaging with a bone anchor installation tool which facilitates the application of a rotative force to said bone anchor means during installation thereof.

16. An arrangement for coupling soft tissue and bone of a living being, the arrangement comprising:

suture anchor means having a first coupling portion for coupling with the soft tissue of the living being, and a resilient engagement means having external threads formed thereon;

bone anchor means having an external portion for engaging with the bone of the living being, and an internal portion for engaging with said resilient engagement means of said suture anchor means, said internal portion of said bone anchor means having internal threads formed therein, said engagement between said internal portion of said bone anchor means and said resilient engagement means being achieved by interengagement between said internal and external threads, said resilient engagement means of said suture anchor means applying a resilient biasing force against said internal portion of said bone anchor means; and an extraction arrangement formed on said resilient engagement means for facilitating the application of a force counter to said resilient biasing force, thereby facilitating disengagement between said suture anchor means and said bone anchor means.

17. The arrangement of claim 16 wherein said resilient engagement means comprises a coupling body for entering into said internal portion of said bone anchor means, and a prong resiliently coupled to said coupling body, said external threads of said resilient engagement means being formed on said prong.

18. An arrangement for coupling soft tissue and bone of a living being, the arrangement comprising:

suture anchor means having a first coupling portion for coupling with the soft tissue of the living being, and a second coupling portion, said second coupling portion having a predetermined coupling portion surface contour, and said first coupling portion being adapted to engage a suture material for effecting the coupling between said first coupling portion and the soft tissue of the living being;

bone anchor means having an external portion for engaging with the bone of the living being, and an internal portion for engaging with said second coupling portion of said suture anchor means, said internal portion having a predetermined internal portion surface contour for engaging with said coupling portion surface contour, whereby said suture anchor means is removably engaged with said bone anchor means;

prong means having an outer surface on which is provided said predetermined coupling portion surface contour;

coupling body means having first and second ends, for coupling at said first end thereof to said suture anchor means; and resilient coupling means for resiliently coupling said prong means and said second end of said coupling body means.

19. The arrangement of claim 18 wherein said suture anchor means and said bone anchor means are arranged to cooperate to apply a friction force to the suture material for securing the suture material.

20. The arrangement of claim 18 wherein said predetermined coupling portion surface contour and said predetermined internal portion surface contour comprise respective interengageable cross-sectionally substantially triangular steps which are interengageable at a sequential plurality of locking positions as said suture anchor means is urged into communication with said bone anchor means.

21. An arrangement for coupling soft tissue and bone of a living being, the arrangement comprising:

suture anchor means having a first coupling portion for coupling with the soft tissue of the living being, and a second coupling portion, said second coupling portion having a predetermined coupling portion surface contour configured as an outer screw thread, and said first coupling portion being adapted to engage a suture material for effecting the coupling between said first coupling portion and the soft tissue of the living being;

bone anchor means having an external portion for engaging with the bone of the living being, and an internal portion for engaging with said second coupling portion of said suture anchor means, said internal portion having a predetermined internal portion surface contour configured as an inner screw thread for engaging with said outer screw threads of said coupling portion surface contour, whereby said suture anchor means is removably engaged with said bone anchor means;

prong means having an outer surface on which is provided said outer screw threads of said predetermined coupling portion surface contour;

coupling body means having first and second ends, for coupling at said first end thereof to said suture anchor means; and resilient coupling means for resiliently coupling said prong means and said second end of said coupling body means.

22. A method of coupling soft tissue and bone of a living being, the method comprising the steps of:

providing a suture anchor and a bone anchor;

threading a suture material through a passageway in a first coupling portion of the suture anchor and through the soft tissue of the living being, for coupling the soft tissue of the living being to the first coupling portion of the suture anchor;

coupling an external portion of the bone anchor with the bone of the living being; and reversibly interengaging a surface contour of a second coupling portion of the suture anchor with an internal surface contour of an internal portion of the bone anchor.

23. The method of claim 22 wherein during the performance of said step of reversibly interengaging there is provided the further step of applying a force to the suture material by compressing same between the suture anchor and the bone anchor.

24. The method of claim 22 wherein said step of coupling an external portion of a bone anchor with the bone of the living being comprises the step of engaging a threaded external surface contour of the bone anchor with the bone of the living being.

25. The method of claim 22 wherein there is provided the further step of decoupling the external portion of the bone anchor from the bone of the living being.

26. The method of claim 22 wherein said step of threading comprises the further step of winding the suture around a portion of the first coupling portion of the suture anchor.

* * * * *